United States Patent
Hack et al.

(10) Patent No.: US 7,278,784 B2
(45) Date of Patent: Oct. 9, 2007

(54) DENTAL X-RAY SYSTEM WITH ELECTRONIC SENSOR

(76) Inventors: Alexander Hack, Kiefernweg 2, D-88400 Biberach (DE); Uwe Zeller, Rissegger Steige 139, D-88400 Biberach (DE); Klaus Weber, Ingoldinger Weg 17, D-88456 Grodt (DE)

( * ) Notice: Subject to any disclaimer, the term of this patent is extended or adjusted under 35 U.S.C. 154(b) by 0 days.

(21) Appl. No.: 11/235,603

(22) Filed: Sep. 26, 2005

(65) Prior Publication Data
US 2006/0067463 A1   Mar. 30, 2006

Related U.S. Application Data

(63) Continuation of application No. PCT/EP2004/003127, filed on Mar. 24, 2004.

(30) Foreign Application Priority Data

Mar. 24, 2003  (DE) ............................... 103 13 043
Nov. 27, 2003  (DE) ............................... 103 55 431

(51) Int. Cl.
*A61B 6/14* (2006.01)
(52) U.S. Cl. ..................... 378/191; 378/98.8
(58) Field of Classification Search ................ 378/191, 378/116, 98.8; 433/29; 250/370.09
See application file for complete search history.

(56) References Cited

U.S. PATENT DOCUMENTS

| | | | | |
|---|---|---|---|---|
| 5,514,873 A | * | 5/1996 | Schulze-Ganzlin et al. | 250/394 |
| 5,781,610 A | * | 7/1998 | Miles | 378/168 |
| 6,307,915 B1 | | 10/2001 | Fröjdh | |
| 6,320,934 B1 | * | 11/2001 | Carroll et al. | 378/98.8 |
| 6,404,852 B1 | | 6/2002 | Petrick et al. | |
| 6,527,442 B2 | | 3/2003 | Carroll | |
| 6,950,496 B2 | * | 9/2005 | Zimmermann et al. | 378/116 |
| 2002/0067407 A1 | * | 6/2002 | Cooper | 348/66 |
| 2002/0154742 A1 | * | 10/2002 | Feldman | 378/191 |

FOREIGN PATENT DOCUMENTS

| | | |
|---|---|---|
| WO | 96/03917 | 2/1996 |
| WO | 00/42491 | 7/2000 |
| WO | 01/22873 A1 | 4/2001 |
| WO | 01/66012 A1 | 9/2001 |
| WO | 02/41783 A1 | 5/2002 |

* cited by examiner

*Primary Examiner*—Edward J. Glick
*Assistant Examiner*—Anastasia S. Midkiff
(74) *Attorney, Agent, or Firm*—Mayback & Hoffman, P.A.; Gregory L. Mayback; Scott D. Smiley

(57) ABSTRACT

A dental X-ray system includes a radiation source used to produce X-rays and disposed in an X-ray head. The system has an electronic sensor used to detect X-rays. The sensor can be detachably connected to a central unit of the X-ray system by a plug-in connection. The electronic control system for the sensor is integrated into a plug connected thereto by an external connection cable and is associated with the sensor, thereby enabling a simple exchange between two sensors. The system can include several sensors that can be operated parallel to each other.

27 Claims, 4 Drawing Sheets

DENTAL X-RAY SYSTEM WITH ELECTRONIC SENSOR

CROSS-REFERENCE TO RELATED APPLICATION

This is a continuing application, under 35 U.S.C. § 120, of copending international application No. PCT/EP2004/003127, filed Mar. 24, 2004, which designated the United States; this application also claims the priority, under 35 U.S.C. § 119, of German patent application No. 103 13 043.8, filed Mar. 24, 2003 and German patent application No. 103 55 431.9, filed Nov. 27, 2003; the prior applications are herewith incorporated by reference herein in their entirety.

BACKGROUND OF THE INVENTION

Field of the Invention

The invention lies in the field of medical devices. The present invention relates to a dental X-ray system for digital X-ray investigations.

Today, to be able to produce a final dental diagnosis, X-ray investigations are essential in dental medicine. Thus, for example, faulty positionings of teeth or damage to the tooth root region often can be recognized only based upon X-ray images. In general, a distinction is made between so-called intra-oral X-ray exposures, in which an X-ray sensitive sensor is brought into the mouth of the patient to be investigated, and panorama exposures, in which the head of the patient is disposed completely between the X-ray head containing the radiation source and a sensor detecting the X-ray radiation.

In the case of intra-oral X-ray exposures, the sensors disposed in the mouth of the patient have a length and width of a few centimeters. Earlier, X-ray films were used as sensors and were enclosed in a plastic sleeve. After exposure of the sensor, the film had to be removed from the pocket and developed until, finally, the result of the X-ray investigation could be observed.

In recent times, classical X-ray films are being increasingly replaced by electronic or digital X-ray sensors. Instead of a radiation sensitive film, there is employed a radiation sensitive semiconductor element, for example, a Charged-Coupled Device (CCD) chip or Complementary Metal-Oxide Semiconductor (CMOS) chip, which is divided into individual image regions (pixels) and detects the X-ray radiation—more precisely stated, the chip detects the X-ray radiation converted to visible light with the aid of a light layer (the so-called scintillator) disposed before the semiconductor element. This light layer is necessary because the semiconductor element is significantly more sensitive for radiation in the visible region than for the X-ray radiation itself. The data issued from the semiconductor chip, then, can be read out by an evaluation unit, which then produces the X-ray image based upon this information. The advantage of this digital process is that the image data arising during imaging is directly available so that, substantially at the same time, the X-ray image can be observed on a monitor or display and the film does not first have to be developed in a complicated manner.

A camera for the production of digital X-ray images is described for example in International publication WO 01/66012 A1, corresponding to U.S. Patent Publication No. 2003/0030721 A1 to Nyholm. This known camera has, as a special feature, a sensor surface that is divided into a plurality of regions, each of which can be drawn on alone for obtaining X-ray data. In particular, the sensor regions can be read out also in parallel.

Even though digital X-ray technology offers many advantages, with respect to conventional classical X-ray technology, a disadvantage arises in that the digital X-ray sensors, in comparison to the classical X-ray films, must be connected with control and evaluation electronics to be able to evaluate the data taken by the sensor. The connection between the sensor and the control and evaluation unit is, thereby, usually carried out with the aid of a cable that is led out of the mouth of the patient and runs to the control and evaluation unit. Beyond this, the control and evaluation electronics must ensure that the digital sensor is read out simultaneously with the activation of the X-ray radiation source so that the system detects or recognizes the complete radiation time and, immediately after switching off of the radiation, makes the image available. The difficulties arising in such a context will first be explained with reference to FIGS. 6 and 7, which illustrate a digital dental X-ray system in accordance with the state of the art. FIG. 6 shows only the X-ray apparatus, while FIG. 7 shows a complete X-ray system including the control and evaluation electronics for the digital sensor.

The X-ray apparatus, designated in FIG. 6 generally with the reference sign 101, has, as a main component, an X-ray head 102 containing the radiation source. The head 102 is moveably connected with a central unit 104, for example, mounted on a wall or ceiling, through a framework 103 of a mounting. The central unit 104 contains, as can be understood from FIG. 7, control electronics 106, which are responsible for the control of the X-ray head 102, in particular, the X-ray radiation source disposed therein. The information necessary for such a purpose is transferred through conductor cables 107 that run within the framework 103. Beyond this, the cables 107 also include the current supply lines for the X-ray radiation source.

The central unit 104 has input elements 105 through which a doctor or other person who operates the X-ray apparatus can enter parameters for the X-ray investigation to be carried out (for example, irradiation time, irradiation duration, tube current (mA), and tube voltage (kV)). Based upon this information, the control electronics 106, then, sends the appropriate signals to the X-ray head 102.

In the case of an X-ray investigation, the radiation coming from the X-ray head 102 is detected by a sensor 108 disposed behind the object to be investigated—which in FIG. 7, is schematically illustrated by a tooth—which sensor has, as a main component, a radiation sensitive semiconductor chip 109 (e.g., CCD or CMOS) that is disposed in a flat housing. The information detected by the CCD or CMOS chip 109 is passed on through a cable 113 to control and evaluation electronics 110, which are disposed in a separate housing 111. The control and evaluation electronics 110 are, on one hand, necessary for the control of the sensor 109 and, on the other hand, evaluate the image information and pass the evaluated information on to a Personal Computing (PC) system 112 on which the digital X-ray image can, then, be observed and archived.

A disadvantage with this classical configuration of a digital X-ray system lies in the fact that, usually, the housing 111 for the control and evaluation electronics 110 of the sensor 108 is disposed independently from the central unit 104 of the X-ray apparatus. Such a configuration has the consequence that the connection cable 113 for the sensor 108 is relatively long and, at least in part, is led through the investigation area. Here, there arises, on one hand, the danger that the cable can come into contact with the floor, which is not desirable for the reasons of hygiene, and, on the other hand, that it represents an obstacle over which a person might trip, whereby the sensor 108 or the electronics located at the sensor connection might be damaged.

A further disadvantage of the separation of central unit 104 of the X-ray apparatus 101 and the control and evaluation electronics 110 for the sensor 108 lies in the fact that an additional cable 114 is necessary. This additional cable 114 runs from the central unit 104 to the housing 111 for the control and evaluation electronics 110 and ensures that the sensor 108 can be read out synchronously with the activation of the X-ray radiation source. This additional cable 114 also represents an obstacle. Although ideas have been followed for triggering the sensor 109 by the sensor radiation itself, these processes are, however, relatively complex and, in comparison with the sending of an activation signal through a cable, ensure no absolute reliability.

To avoid the problems indicated above, it is already known from International publication WO 96/03917 A1 to Eichhorn et al. to integrate a part of the control and evaluation electronics for the digital sensor into the central unit of the X-ray apparatus and to allow the lines between the sensor and the electronics to, in large part, run within the framework. Then, at the X-ray head, itself, there is located a plug socket into which there can be connected an appropriate external connection cable that leads to the digital sensor. The advantage of such a variant lies in the fact that the external connection cable for the sensor is significantly shorter than in the case of the system illustrated in FIG. 7, so that this cable no longer represents an obstacle for persons within the investigation area.

An exchange between different sensors is also made possible with an X-ray system known from International publication WO 02/41783 A1, corresponding to U.S. Pat. Nos. 6,527,442 to Seamus, 6,404,852 to Seamus et al., 6,320,934 to Seamus et al., and 6,307,915 to Froejdh, with which digital X-ray sensors can be connected directly to a PC with the aid of a plug. The plug has, for this purpose, internal electronics through which reception and further processing of signals received from the sensor is effected.

Finally, U.S. Pat. Publication No. 2002/0067407 A1 to Cooper describes a dental X-ray system with which digital sensors are connected to a central facility. For such a purpose, a special interface is provided that is inserted into a corresponding port of the central apparatus. However, the precise functioning of the interface is not described.

SUMMARY OF THE INVENTION

It is accordingly an object of the invention to provide a dental X-ray system with electronic sensor that overcomes the hereinafore-mentioned disadvantages of the heretofore-known devices of this general type and that provides a dental X-ray system that makes it possible for the dentist to flexibly put to use digital sensors of different sizes or configurations.

With the foregoing and other objects in view, there is provided, in accordance with the invention, a dental X-ray system, including an X-ray head having a radiation source selectively generating X-ray radiation, a central unit, a plug connection connected to the central unit, and an electronic X-ray radiation detection sensor releasably connected with the central unit through the plug connection. The sensor has a plug, control electronics integrated into the plug, and an external cable connecting the plug with the sensor.

With the objects of the invention in view, there is also provided a dental X-ray system, including an X-ray head having a radiation source selectively generating X-ray radiation, a central unit, and first and second electronic X-ray radiation detection sensors releasably connected with the central unit through at least one plug connection. The sensors operate in parallel to one another. Each of the sensors has a plug, control electronics integrated into the plug, and an external cable connecting the plug with the sensor.

With the objects of the invention in view, there is also provided a dental X-ray system, including an X-ray head having a radiation source selectively generating X-ray radiation, a central unit connected to the X-ray head and controlling X-ray radiation generated from the X-ray head, an electronic X-ray radiation detection sensor having an X-ray detector for detecting generated X-ray radiation data, a connection plug with integrated detector control electronics connected to the X-ray detector for controlling the X-ray detector, and a cable connecting the connection plug with the X-ray detector. The central unit and/or the sensor has a plug connection releasably connecting the sensor with the central unit for transmitting sensed X-ray radiation data to the central unit.

With the objects of the invention in view, in combination with a dental X-ray system having an X-ray head with a radiation source selectively generating X-ray radiation and a central unit connected to the X-ray head and controlling X-ray radiation generated from the X-ray head, there is also provided a removable sensing unit, including an electronic X-ray radiation detection sensor having an X-ray detector for detecting generated X-ray radiation data, a connection plug with integrated detector control electronics connected to the X-ray detector for controlling the X-ray detector, a cable connecting the connection plug with the X-ray detector, and a plug connection to be electrically connected to the central unit and releasably connecting the connection plug of the sensor with at least one of the X-ray head and the central unit and transmitting sensed X-ray radiation data to the central unit.

The present invention relates primarily to integration of control and evaluation electronics into an X-ray apparatus.

In accordance with a first aspect of the present invention, the dental X-ray system includes an X-ray apparatus having an irradiation source for generating X-ray radiation, disposed in an X-ray head, and of an electronic sensor for detecting the X-ray radiation, wherein the sensor can be releasably connected with the central unit of the X-ray system through a plug connection. Thereby, in accordance with the invention the control electronics for the digital sensor is integrated into the plug.

Thus, in comparison to the known state of the art, the present invention goes a step further, as the control electronics necessary for the operation of the sensor are moved into the plug connection of the cable that leads to the digital sensor. Such a configuration is possible because, in the meantime, the appropriate control electronics for the semiconductor chip of the sensor, e.g. the so-called CCU (CCD control unit), or the electronics for the control of a CMOS chip can be so miniaturized that they take up only very little space. There is, thus, the possibility of so configuring these electronic components that they take up the size of half a matchbox and are only a few millimeters high. The supply side connection for the plug can, then, for example, be integrated into the X-ray head or the framework in the immediate vicinity of the head of the X-ray apparatus.

The advantage of the configuration of the control electronics in the connection cable for the digital sensor lies in the fact that the sensor with the associated electronics can be removed as a simple component unit and replaced by a new combination so that, in principle, for each digital sensor employed, suitable control electronics are present. For the dentist, it is possible through this, without great effort, to change the sensors and, for example, employ a new sensor with greater dimensions.

In accordance with another feature of the invention, there are provided a mounting having a framework carrying the X-ray head and a connection socket for receiving the plug, the connection socket being disposed in one of the X-ray head and the framework in an immediate vicinity of the X-ray head.

Furthermore, preferably, there is provided a connection line, through which the control electronics for the digital sensor is informed at what time point the X-ray radiation source is activated, so that the sensor can be automatically read out synchronously.

In accordance with a further feature of the invention, there is provided at least one connection line running within the framework from the connection socket to the central unit.

In accordance with an added feature of the invention, there is provided a repository for removably receiving the sensor thereat, the repository being disposed on at least one of the X-ray head and the framework.

A further development of the present invention relates to storage of the sensor or sensors. Thus, there is provided, preferably directly at the X-ray head, a repository for the sensor that, in accordance with a particularly preferred exemplary embodiment, is configured to be removable and sterilizable. In such a context, it is to be taken into consideration that, before use, the sensor usually is provided with a disposable sleeve and/or a holder system and, then, a plurality of exposures made one after another. If the procedure has to be interrupted, there must also be the possibility of quickly putting the sensor to one side. Here, however, the repository is contaminated. Therefore, it must be cleaned and sterilized, which is facilitated by the removable configuration.

In accordance with an additional feature of the invention, the plug connection has a Universal Serial Bus (USB) connection.

In accordance with yet another feature of the invention, the control electronics integrated into the plug is a USB device.

In accordance with yet a further feature of the invention, the plug connection is a standard PC connection, preferably, at least one of a USB connection, a FIREWIRE® connection, and a BLUETOOTH® connection.

In accordance with yet an added feature of the invention, preferably, the X-ray radiation source and the sensor and its control electronics are supplied from a common current source. The current supply source can commonly supply current to the X-ray head, the central unit, the sensor, and/or the control electronics.

In accordance with yet an additional feature of the invention, the sensor is read out synchronously with an activation of the X-ray radiation source.

In accordance with again another feature of the invention, the central unit has a signal unit electrically connected to the sensor and transmitting a start signal to the control electronics upon activation of the radiation source.

In accordance with again a further feature of the invention, the plug connection has a USB connection and the signal unit has a USB hub.

In accordance with again an added feature of the invention, the sensor transmits data and a computing device is connected to the sensor and/or the central unit and is programmed to evaluate the data transmitted by the sensor.

In accordance with again an additional feature of the invention, the sensor transmits the data to the computing device wirelessly, through a data network, or through a memory media.

In accordance with still another feature of the invention, the sensor has a flat housing and a radiation sensitive semiconductor element mounted in the housing.

In accordance with still a further feature of the invention, the radiation sensitive semiconductor element is a CCD chip and/or a CMOS chip.

In accordance with a concomitant feature of the invention, a simple exchange between two sensors of different sizes is made possible because the X-ray system is equipped with a plurality of different sensors which, during an X-ray exposure, can be read out at the same time. The sensors carry out sensor operations at the same time. The control and evaluation electronics of the sensors automatically recognize which sensor is disposed in the radiation field of the X-ray radiation. Alternatively, there is also the possibility of transmitting the detected image data of both sensors to a PC and to carry out with the aid of appropriate software a decision as to which image data is relevant.

The user of the X-ray system can, thus, freely choose between the available sensors and need not first send to the apparatus information with regard to the type of sensor being employed.

Instead, the system automatically recognizes, based upon the transmitted data, which sensor is being employed at the moment, through which a particularly simple operation is made possible.

Other features that are considered as characteristic for the invention are set forth in the appended claims.

Although the invention is illustrated and described herein as embodied in a dental X-ray system with electronic sensor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

In the figures of the drawings, unless stated otherwise, identical reference symbols denote identical parts.

Figure 2:
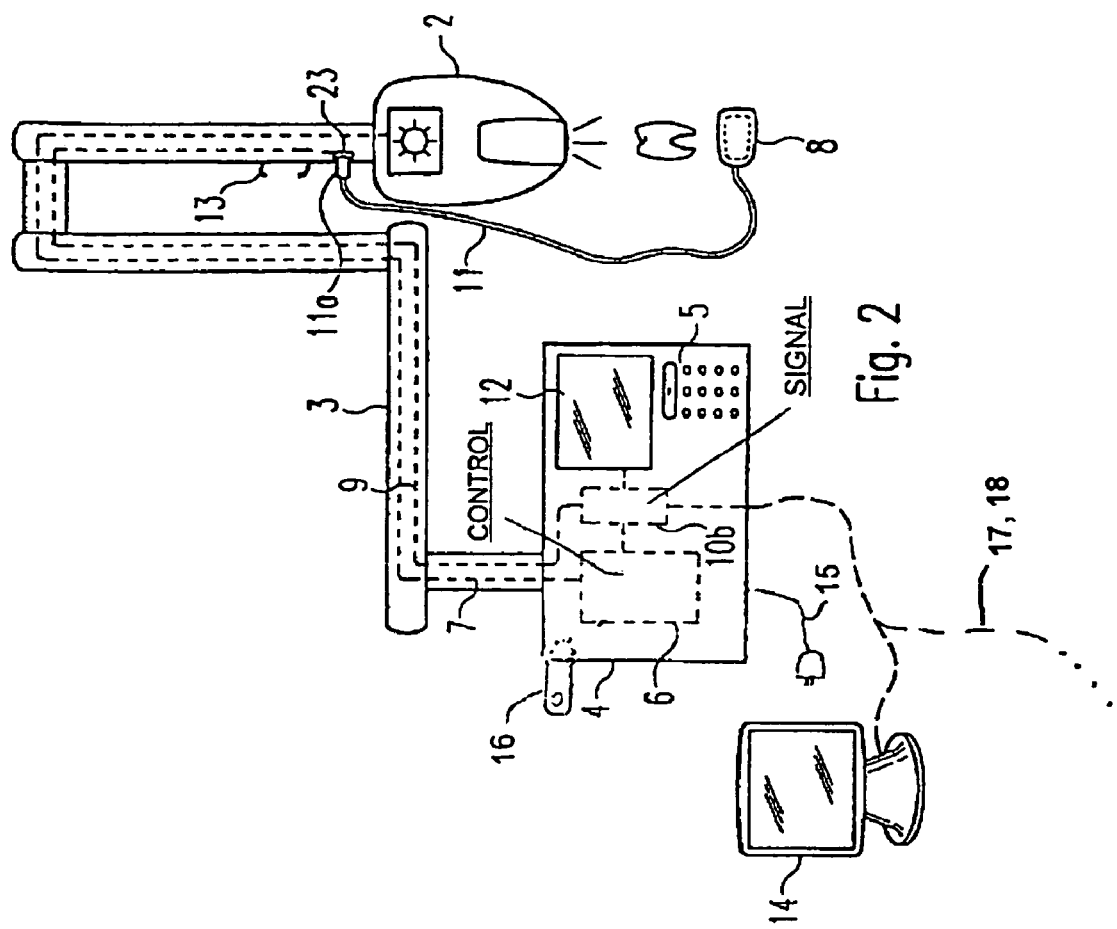
FIG. 2 is a partially hidden, diagrammatic side elevational view of the X-ray system of FIG. 1.
Figure 1:
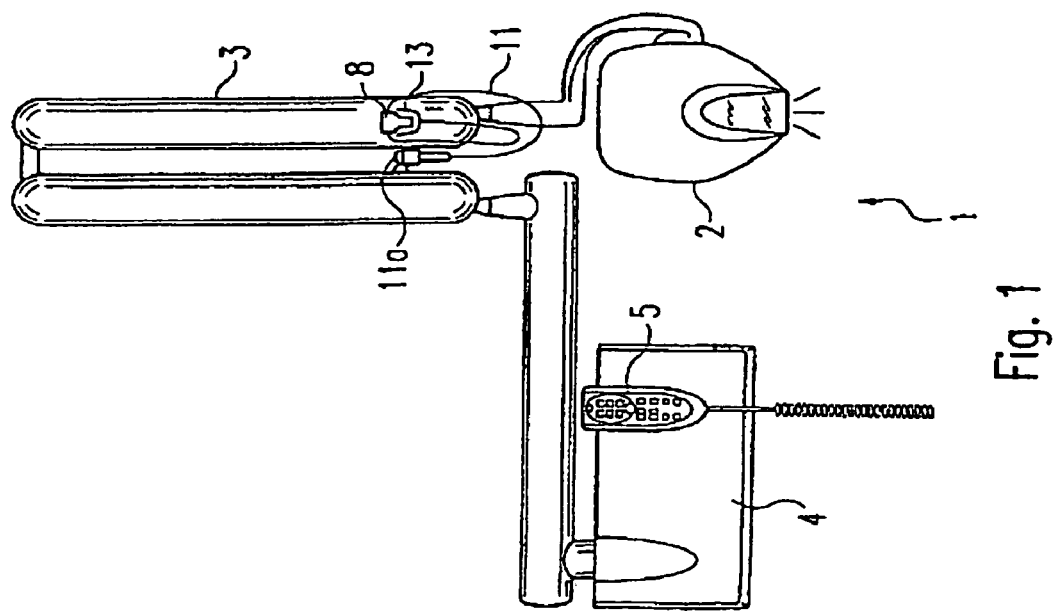
FIG. 1 is a diagrammatic side elevational view of a first exemplary embodiment of a dental digital X-ray system according to the invention.

Referring now to the figures of the drawings in detail and first, particularly to FIGS. 1 and 2 thereof, there is shown an X-ray system 1 having an X-ray head 2 containing the X-ray radiation source. The X-ray head 2 is connected with a central unit 4 through a framework 3 of a mounting. In the illustrated exemplary embodiment, the central unit 4 is mounted on a wall; it could, however, just as well be attached to a ceiling of the investigation area or be configured as a separate console. On the outside of the central unit 4 there are disposed input elements 5 for the input of desired investigation parameters (e.g., irradiation time, irradiation duration, tube current (mA), tube voltage (kV), etc.). Internally, the central unit 4 has a control unit 6 that is responsible for the control of the X-ray radiation source in the X-ray head 2 (shown diagrammatically in FIG. 2) and, for such a purpose, is connected therewith through a line 7 running through the framework 3.

A significant feature of the X-ray system in accordance with the invention is that the X-ray sensor 8 is, now, no longer connected with a separate housing, but, instead, is connected at a plug socket 23 through a relatively short cable 11. The plug socket 23 is disposed, for example, in the framework 3 in an immediate vicinity of the X-ray head 2. From such a configuration, there arises the advantage that the connection cable 11 for the sensor 8 is relatively short and no longer runs as an obstacle through the investigation area. The short length of the cable 11 has, beyond this, the advantage that the X-ray sensor 8 can no longer fall to the floor and, thereby, be damaged. In the illustrated example, there is further provided on the framework 3 a repository 13 in which the sensor 8 can be placed when not in use.

Figure 3:
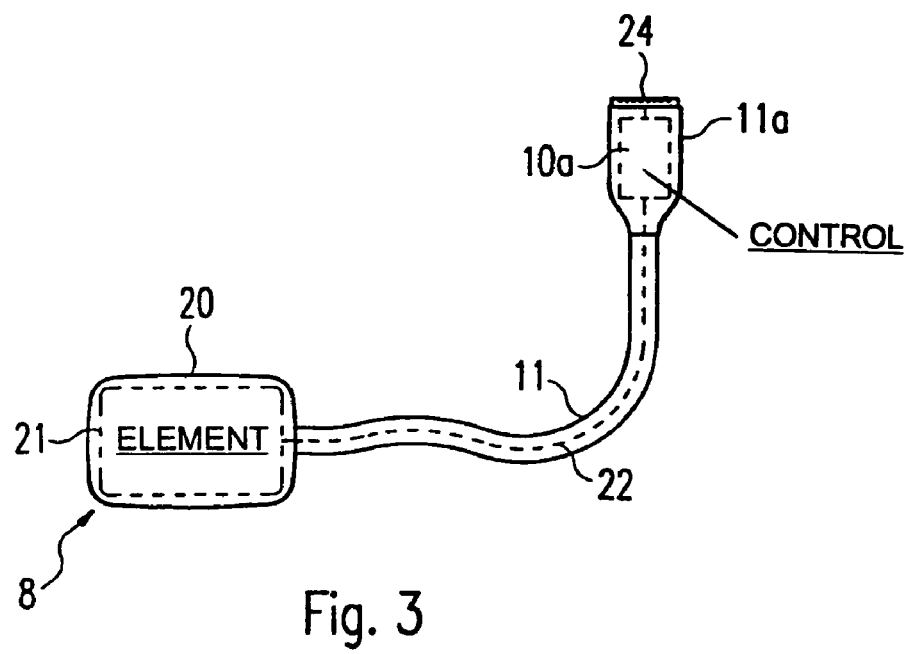
FIG. 3 an enlarged, partially hidden, plan view of an exemplary embodiment of a digital sensor and an associated connection cable of FIG. 1.

For control of the digital sensor 8 there is, in turn, any needed and/or appropriate electronics. In accordance with the present invention, however, these control electronics 10a are now integrated into the cable 11, more precisely, into the connection plug 11a of the cable 11, as is illustrated in more detail in FIG. 3.

The sensor 8, which is, in substance, an X-ray radiation sensitive semiconductor element 21 (a CCD chip or CMOS chip) that is disposed in a flat, rectangular shaped housing 20, and is, thereby, controlled through control electronics 10a disposed within the plug 11a at the end of the cable 11 remote from the sensor 8. The control electronics 10a that regulate the control of the semiconductor element 21 and the read out of image information are connected with the semiconductor element 21 through a plurality of lines 22 that run within the cable 11. Due to the possibility that now arises for miniaturization of such electronic elements, the control electronics 10a has such slight dimensions that it can be integrated into the plug 11a without great effort. The trigger signals delivered externally, i.e., from the central unit 4, to the control electronics 10a for activation of the sensor 8 or the image information received and to be transmitted by the sensor 8 are, then, passed on through appropriate connection contacts 24 of the plug 11a.

Figure 7:
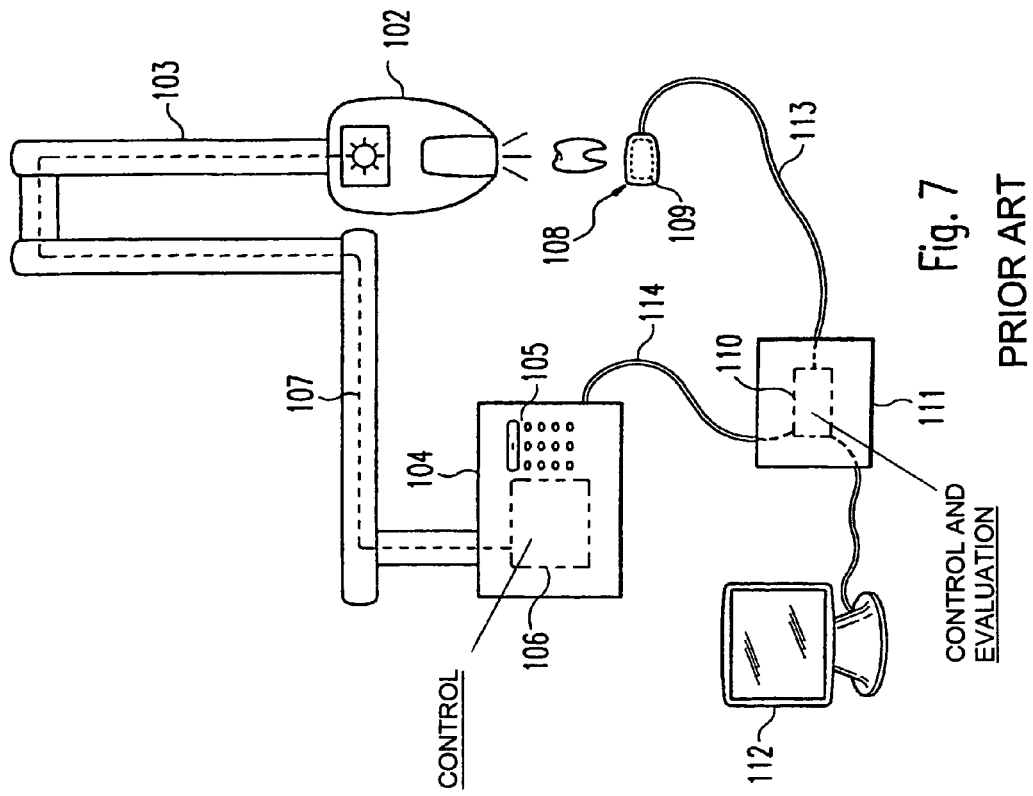
FIG. 7 a partially hidden, diagrammatic side elevational view of the prior art X-ray system of FIG. 6.
Figure 6:
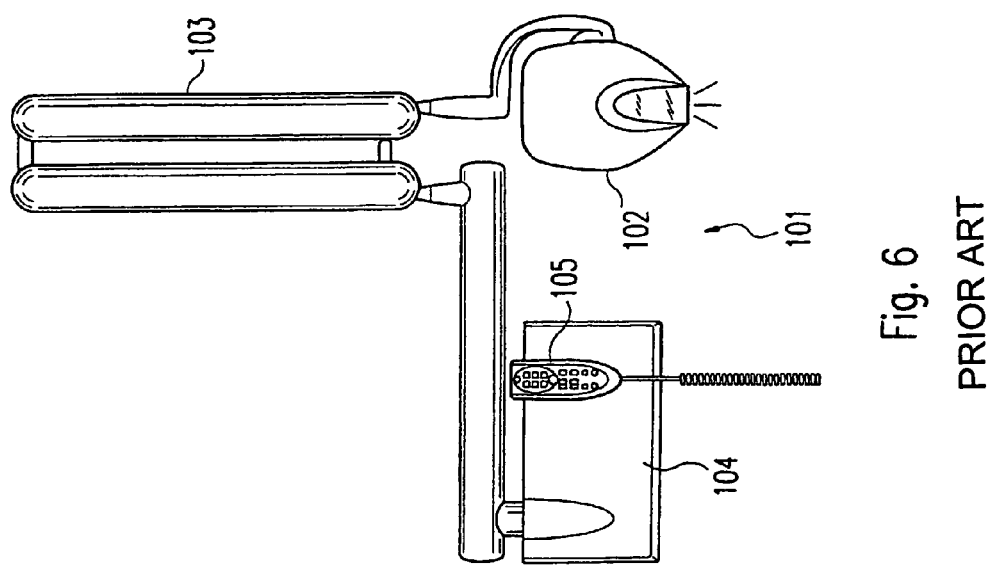
FIG. 6 is diagrammatic side elevational view of a prior art X-ray apparatus.

Of significance is that, through the integration of the control electronics 10a into the plug 11a, further electronic components that are involved in the control of the sensor 8, for example, the electronics provided with reference sign 110 in FIG. 7, can be omitted. Therefore, the sensor 8 may, for example, also be directly connected to a PC or a PC peripheral device (e.g., a USB hub). Through such a configuration, the subject of the present invention differs from already known systems in which, although a part of the electronics of the sensor is integrated into the plug, they still however depend on further external electronics for the operation of the sensor.

Preferably, a standardized system is used for the plug 11a and/or connection contacts 24, which makes a large number of plug cycles possible. For such a purpose, for example, USB connections or metallic round connectors suggest themselves for the contacts 24. However, connections in accordance with other PC standards can also be used, in particular, the so-called FIREWIRE® or BLUETOOTH® connection. Furthermore, the plug 11a may also contain the lines for the possibly necessary current supply of the sensor 8, whereby, preferably, the X-ray radiation source and the sensor 8 are supplied from the same current supply source. A current supply source 15, e.g., a battery or an electric mains, is diagrammatically shown in FIG. 2.

In accordance with a particularly preferred exemplary embodiment, the plug 11a or plug socket 23 is formed as a USB connection and the control electronics 10a for the sensor 8 contained therein represent a USB device. Here, however, it is to be taken in consideration that, for a USB path, presently, a maximum length of 5 m is allowed and, otherwise, the employment of an amplifier—a so-called USB hub—is necessary. Such a limitation is envisioned not to always be a requirement, however. Because the arm lengths of the framework 3 and, thus, the length of the connection cable between the plug 11a and the central unit, is about 3 meters, presently, a USB hub is preferably provided to ensure reliable data traffic, which, for example, may be a component of the unit 10b to be described below. In such a context, it is to be noted that it is already known from U.S. Pat. No. 6,134,298 to Schick et al. to connect an intra-oral digital sensor to a computer by a USB connection. However, with the Schick et al. system, there is no suggestion regarding the control electronics, in particular, Schick et al. does not disclose or suggest placing the control electronics for the sensor in the plug.

Even when the control of the sensor 8 is carried out through the control electronics 10a integrated into the plug 11a, external trigger signals must, nonetheless, be transmitted to the electronics 10a, which trigger signals initiate a read out of the semiconductor chip 21 of the sensor 8. For such a purpose, there is provided, within the central unit 4 of the X-ray apparatus, a signal unit 10b that is connected with the control unit 6 for the X-ray head 2 or for the X-ray radiation source and, upon an activation of the X-ray radiation source, automatically transmits a start signal to the control electronics 10a for the sensor 8 that initiates a readout of the image information. For such a purpose, the unit 10b is connected with the control electronics 10a through a line 9 likewise running through the framework 3. The connection between the unit 10b and the control unit 6 for the X-ray apparatus or the X-ray radiation source also has the advantage of making possible a bidirectional data exchange, which makes possible an optimal matching between a sensor system and an X-ray radiation generator with regard to the duration and strength of the exposure during an investigation.

In such a context, it is important that the signal unit 10b communicates exclusively with the control electronics 10a to ensure a read out of the sensor 8 synchronously with the X-ray radiation. However, the signal unit 10b is not involved in the control of sensor 8 itself. Furthermore, the unit 10b also may be responsible for evaluation of the image information that is transmitted from the sensor 8 or from its control electronics 10a. Such image information may, for example, be passed on directly to a display 12, which, in the case of the exemplary embodiment illustrated in FIG. 2, is likewise integrated into the central unit 4 of the X-ray system. Alternatively, the image information transmitted from the sensor 8 or its control electronics 10a can be passed on from the unit 10b, even without further processing, to an external PC system 14 or a central data processing system of the practice or the hospital 17 and, there, the image information is processed, observed, and archived. Here, the USB hub provided, if appropriate, in the unit 10b can also be put to use. The connection between the X-ray system 1 or the central unit 4 and the external PC system 14 may, thereby—as illustrated—be effected through a cable that, if appropriate, is a component of a hospital internal network 18. There also exists the possibility of transmitting the data in a wireless manner, e.g. in accordance with the BLUETOOTH® standard. A different possibility for the transmission of the data lies also in intermediately storing the data at the central unit 4 in a memory medium 16 and, then, reading out the memory medium on the PC system, whereby, in such a solution in particular, the employment of so-called memory sticks or other known memory cards suggests itself.

The advantage of the integration of the control electronics 10a into the plug 11a of the connection cable 11 for the sensor 8 lies in the fact that the sensor 8 and the associated electronics 10a, to a certain extent, form a unit, optimally matched to one another. If another sensor is to be employed, this can be effected through an exchange of the connection cable, through which, at the same time, control electronics matched to the new sensor are connected.

In this manner, a change between sensors of different kinds and sizes can be effected simply and rapidly. The unit 10b of the central apparatus 4 of the X-ray system, in turn, makes possible, without great outlay, a synchronous triggering of the sensor 8 upon an activation of the X-ray radiation source. An additional external connection cable between the control unit for the X-ray generator and the control electronics for the sensor is likewise no longer necessary.

Figure 4:
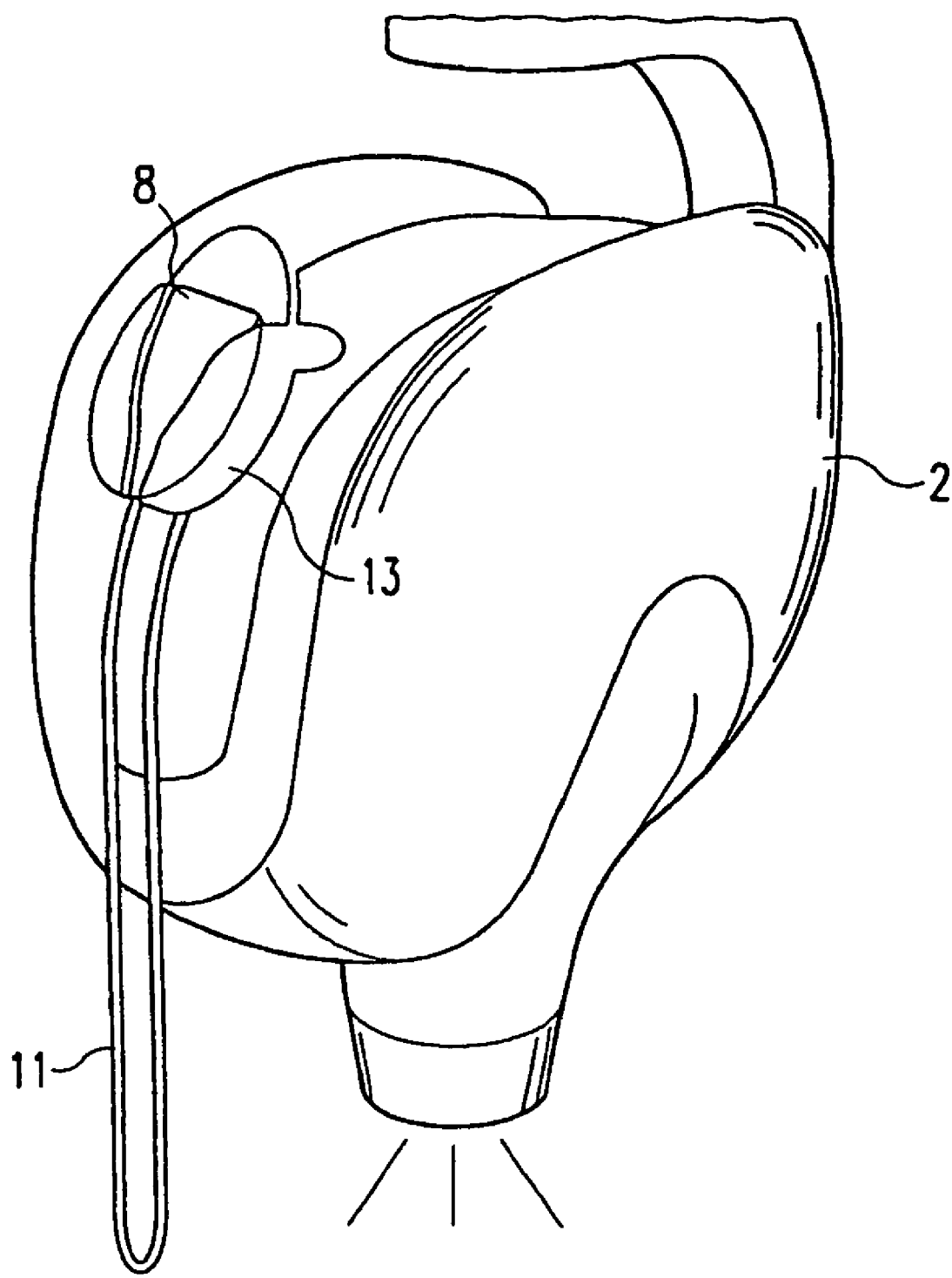
FIG. 4 a fragmentary, enlarged perspective view of a second exemplary embodiment of an X-ray head according to the invention.

FIG. 4 shows a particularly preferred exemplary embodiment for an X-ray head 2 which distinguishes itself by being able to directly connect the sensor 8 to the X-ray head 2 with its cable 11. For such a purpose, there is provided a plug socket in the housing of the X-ray head 2. The plug socket is disposed below the repository 13 for the sensor 8 and, correspondingly, is not seen in the illustration of FIG. 4. With regard to the technical configuration of the connection for the sensor 8, the illustrated exemplary embodiment is similar to the exemplary embodiment of FIGS. 1 and 2, i.e. the plug is, again, preferably constituted as a USB device, but may also be a FIREWIRE® connection or a connection in accordance with another PC standard.

A further special feature for the second exemplary embodiment lies in configuring the repository 13 for the sensor 8 to be removable and sterilizable. Here, it is to be taken into consideration that, before use, the sensor 8 is usually provided with a disposable covering and/or holder system and, then, a plurality of exposures are made one after another. If the sequence must be interrupted, the possibility must be available of quickly placing the sensor 8 to one side. If the sensor 8 is placed in the repository 13 in such a case, the repository 13 could be contaminated to require cleaning and sterilizing of the repository 13. A removable configuration of the repository 13 and the employment of a sterilizable material for the repository 13 takes account of this situation. Of course, the removable and sterilizable configuration of the repository 13 can also be provided in the case of other exemplary embodiments of the present invention.

Figure 5:
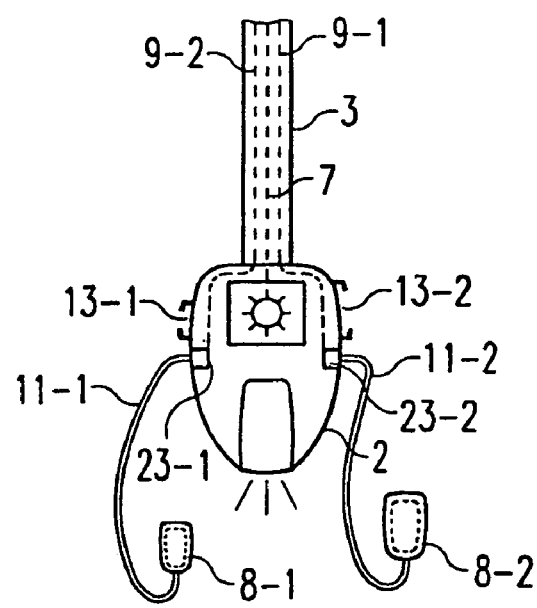
FIG. 5 is a fragmentary, partially hidden, diagrammatic, side elevational view of an alternative configuration of the X-ray system of FIGS. 1 and 2.

FIG. 5 shows a further alternative configuration in accordance with the second aspect of the present invention, which likewise makes possible a change between two sensors 8-1, 8-2 that can be carried out easily and rapidly.

In the illustrated example, the X-ray head 2 has two connections 23-1 and 23-2 for two connection cables 11-1, 11-2 with corresponding sensors 8-1, 8-2. The sensors 8-1, 8-2, which, in the illustrated exemplary embodiment differ with regard to their size, are each connected with the unit 10b disposed in the central unit 4 through their own line 9-1 or 9-2 running in the framework 3 and are capable of reading out and transmitting data in parallel. Preferably, as in the exemplary embodiments illustrated in FIGS. 1 to 4, the control electronics for the sensors 8-1 and 8-2 is integrated into the connection cables 11-1, 11-2 or plugs.

In the case of the exemplary embodiment according to FIG. 5, the special feature lies in the unit 10b for evaluation of the signals of both sensors 8-1 and 8-2 automatically recognizing, based upon the data transmitted from the sensors 8-1, 8-2 or their control electronics, which of the two sensors 8-1 or 8-2 is exposed to X-ray radiation. If, in such a case, an X-ray exposure is to be effected, the user of the X-ray system can freely select one of the two sensors 8-1 or 8-2, without having to previously manually input which X-ray sensor is to be employed. Instead, the user can place the selected sensor directly into the mouth of the patient and carry out the X-ray exposure because the image information of the exposed sensor will be detected automatically by the evaluation unit and presented on the display.

Alternatively, there is also a possibility of passing on both sensor signals to an external PC system and only there—if appropriate with the support of suitable software—determining which sensor signals should be employed finally. Further, it is to be remarked that it is not compulsory for both sensor cables 11-1 and 11-2 to be connected to the plug socket(s) 23-1, 23-2 disposed on the X-ray head 2 or framework 3. There is also a possibility of directly connecting one of the two sensors 8-1, 8-2, which, for example, is less frequently employed, directly to the external PC system.

The illustrated exemplary embodiments of the present invention, thus, open up the possibility of selecting in a simple manner between a plurality of desired sensors, or of replacing one sensor by another. With such possibilities, the invention contributes to the making possible of a particularly simple handling of the overall X-ray system.

We claim:

1. A dental X-ray system, comprising:
   an X-ray head having a radiation source selectively generating X-ray radiation;
   a central unit communicating with said X-ray head to selectively control the generation of X-ray radiation from said X-ray head;
   a plug connection connected to said central unit; and
   an electronic X-ray radiation detection sensor releasably connected with said central unit through said plug connection, said sensor having:
   a plug;
   control electronics integrated into said plug, said control electronics regulating control of said X-ray radiation detection sensor and regulating reading out of image information from said X-ray radiation detection sensor; and
   an external cable connecting said plug with said sensor.

2. The dental X-ray system according to claim 1, further comprising:

a mounting having a framework carrying said X-ray head; and a connection socket for receiving said plug, said connection socket being disposed in one of said X-ray head and said framework in an immediate vicinity of said X-ray head.

3. The dental X-ray system according to claim 2, further comprising at least one connection line running within said framework from said connection socket to said central unit.

4. The dental X-ray system according to claim 2, further comprising a repository for removably receiving said sensor thereat, said repository being disposed on at least one of said X-ray head and said framework.

5. The dental X-ray system according to claim 4, wherein said repository is removable.

6. The dental X-ray system according to claim 4, wherein said repository is of a sterilizable material.

7. The dental X-ray system according to claim 1, wherein said plug connection has a USB connection.

8. The dental X-ray system according to claim 7, wherein said control electronics integrated into said plug is a USB device.

9. The dental X-ray system according to claim 1, wherein said plug connection is a standard PC connection.

10. The dental X-ray system according to claim 9, wherein said standard PC connection is selected from one of the group consisting of a USB connection, a Firewire connection, and a Bluetooth connection.

11. The dental X-ray system according claim 1, further comprising a current supply source commonly supplying current to each of said X-ray head, said central unit, said sensor, and said control electronics.

12. The dental X-ray system according claim 1, wherein detection by said sensor occurs synchronously with activation of said radiation source.

13. The dental X-ray system according to claim 12, wherein said central unit has a signal unit electrically connected to said sensor and transmitting a start signal to said control electronics upon activation of said radiation source.

14. The dental X-ray system according to claim 13, wherein said plug connection has a USB connection and said signal unit has a USB hub.

15. The dental X-ray system according to claim 1, wherein:
said sensor transmits data; and
a computing device is:
connected to at least one of said sensor and said central unit; and
programmed to evaluate said data transmitted by said sensor.

16. The dental X-ray system according to claim 15, wherein said sensor transmits said data to said computing device wirelessly.

17. The dental X-ray system according to claim 15, wherein said sensor transmits said data to said computing device through a data network.

18. The dental X-ray system according to claim 15, further comprising memory media, said sensor transmitting said data to said computing device through said memory media.

19. The dental X-ray system according to claim 1, wherein said sensor has a flat housing and a radiation sensitive semiconductor element mounted in said housing.

20. The dental X-ray system according to claim 19, wherein said radiation sensitive semiconductor element is one of a CCD chip and a CMOS chip.

21. The dental X-ray system according to claim 1, wherein said sensor is at least two sensors carrying out sensor operations at the same time.

22. The dental X-ray system according to claim 21, wherein:
said electronic X-ray radiation detection sensors detect signals; and
said central unit has a unit automatically recognizing which of said sensors is in a field of X-ray radiation based upon signals detected by said sensors.

23. The dental X-ray system according to claim 21, wherein said central unit has a recognition unit automatically recognizing which of said sensors is in a field of X-ray radiation based upon X-ray radiation detected by said sensors.

24. The dental X-ray system according to claim 21, wherein said at least two sensors are different in size.

25. A dental X-ray system, comprising:
an X-ray head having a radiation source selectively generating X-ray radiation;
a central unit communicating with said X-ray head to selectively control the generation of X-ray radiation from said X-ray head; and
first and second electronic X-ray radiation detection sensors releasably connected with said central unit through at least one plug connection, said sensors operating in parallel to one another, each of said sensors having:
a plug;
control electronics integrated into said plug, said control electronics regulating control of said X-ray radiation detection sensor and regulating reading out of image information from said X-ray radiation detection sensor; and
an external cable connecting said plug with said sensor.

26. The dental X-ray system according to claim 25, wherein:
said electronic X-ray radiation detection sensors detect signals; and
said central unit has an evaluation unit automatically recognizing which of said sensors is in a field of X-ray radiation based upon signals detected by said sensors.

27. The dental X-ray system according to claim 25, wherein said central unit has an evaluation unit automatically recognizing which of said sensors is in a field of X-ray radiation based upon X-ray radiation detected by said sensors.

* * * * *